(12) United States Patent
Roederer et al.

(10) Patent No.: US 9,663,812 B2
(45) Date of Patent: May 30, 2017

(54) ADAPTER FOR SUSPENDING A CRYOVIAL OVER A CENTRIFUGE TUBE

(71) Applicant: The United States of America, as represented by the Secretary, Department of Health & Human Services, Washington, DC (US)

(72) Inventors: Mario Roederer, Bethesda, MD (US); Margaret H. Beddall, Washington, DC (US); Pratip K. Chattopadhyay, Elkridge, MD (US)

(73) Assignee: The United Stated of America, as represented by the Secretary, Department of Health & Human Services, Washington, DC (US)

( * ) Notice: Subject to any disclaimer, the term of this patent is extended or adjusted under 35 U.S.C. 154(b) by 0 days.

(21) Appl. No.: 14/661,449

(22) Filed: Mar. 18, 2015

(65) Prior Publication Data

US 2016/0274004 A1   Sep. 22, 2016

(51) Int. Cl.
*B04B 1/00* (2006.01)
*C12Q 1/02* (2006.01)
*B01L 3/00* (2006.01)

(52) U.S. Cl.
CPC .............. *C12Q 1/02* (2013.01); *B01L 3/5021* (2013.01); *B01L 2200/026* (2013.01); *B01L 2300/042* (2013.01); *B01L 2300/047* (2013.01)

(58) Field of Classification Search
CPC ......................................................... B01L 3/14
See application file for complete search history.

(56) References Cited

U.S. PATENT DOCUMENTS 5,501,841 A * 3/1996 Lee .......................... B01L 3/502
422/506

\* cited by examiner

*Primary Examiner* — Jyoti Nagpaul
(74) *Attorney, Agent, or Firm* — Locke Lord LLP; Scott D. Wofsy (57) ABSTRACT

A system is disclosed for thawing a frozen specimen that includes a cryovial containing a frozen specimen, a centrifuge tube containing a medium, and an adaptor for suspending the cryovial over the centrifuge tube in an inverted position, wherein the adaptor has an elongated tubular body defining opposed proximal and distal ends, and it has an axial bore extending from the distal end thereof to the proximal end thereof to define an outer periphery and an inner periphery, and wherein the outer periphery is dimensioned for insertion into the centrifuge tube and the inner periphery is dimensioned to receive the cryovial in an inverted position.

12 Claims, 6 Drawing Sheets

ADAPTER FOR SUSPENDING A CRYOVIAL OVER A CENTRIFUGE TUBE

BACKGROUND OF THE INVENTION

1. Field of the Invention

The subject invention is directed to a device and system that expedites and automates thawing of viably frozen cells, and more particularly, to an adaptor for supporting or otherwise suspending a cryovial containing a cryopreserved sample of viable cells over a centrifuge tube containing a cell culture medium.

2. Description of Related Art

The preservation of cells is an extremely important aspect of cell culture and fundamental to biological research. The only effective means of viably preserving eukaryotic cells is by freezing, also known as cryopreservation, that can be accomplished with either liquid nitrogen or by employing cryogenic freezers. The freezing process involves slowly reducing the temperature of prepared cells to −30° C. to −60° C. followed by a transfer to temperatures less than −130° C. Once at ultralow temperatures, the cells are biologically inert and can be preserved for years.

Cryopreserving eukaryotic cells differs from preserving bacteria and fungi in that higher viability is required. Where a 1% survival rate of a microbial culture can be practical, such low viability is unacceptable with cultured cells. High survival rates may be very important for cell lines due to the expense and difficulty in preparation, slow relative rate of growth, and tendency to change with repeated passage in culture. In addition, in many cases expansion of cryopreserved cells is not possible—for example, when working with cells isolated from blood or tissue specimens. Consequently, methods used for cell culture cryopreservation must ensure high viability (e.g., >80%).

Another important criterion is the overall yield (i.e., cells recovered after thawing compared to cells frozen). In particular, cells from tissue specimens are highly valuable and comprise a limiting resource. Maximizing yield of viably recovered cells is paramount.

Finally, the variability in these values must minimized. Differential viability and yield are known to impact assays performed following cell thawing. In particular, assays performed in GLP clinical laboratory settings place a high premium on minimizing the variability; in some settings, small decrements in viability or yield are tolerated to achieve lesser variation.

Factors that can affect the viability of cryopreserved cells include growth conditions prior to harvesting, the physiological state of the cells, the cell density, choice of cyroprotectant, and handling techniques. For cells isolated from tissues, there is no choice for most of these, and handling techniques become the principal source of variability. Cyroprotectants such as DMSO are valuable to prevent cell lysis during the freezing process. The diffusion of cryoprotective agents into a cell will result in a partial replacement of intracellular water and help to prevent dehydration (from ice formation) during freezing. Glycerol is also known to stabilize proteins in their native states and to assist in the maintenance of critical macromolecular interactions at subzero temperatures.

Nearly every cell biology laboratory will thaw cryopreserved specimens at some point in time, with large networks of vaccine or disease pathogenesis laboratories thawing thousands of cryopreserved cell specimens every year. In recent years, as technology has become available to measure more parameters from a single specimen, the size of immunological studies has grown greatly. A well-powered study can require tens of thousands of samples, and although high-throughput devices have been developed for automated acquisition of data, thawing cryopreserved specimens remains a labor-intensive, low-throughput endeavor.

The common method involves partially submerging cell vials in a 37° C. water bath, and then "swirling" the vials so that heat is evenly distributed, until only a "pea-sized" ice crystal remains. Because this is an intricate process, no more than four vials can be thawed at a time, severely limiting throughput. The subjective nature of the process also introduces problems, as the duration of the water bath step can vary dramatically from thaw to thaw, researcher to researcher, or by number of vials. This has important consequences for downstream assays, since incomplete thawing results in poor cell recovery, while excessive thawing time decreases cell viability. Additionally, the exposure of vials to an open 37° C. water bath increases the possibility of bacterial/fungal contamination.

There is a need for a system and method for expediting and automating thawing of cryopreserved specimens that overcomes the deficiencies and limitations of prior art systems and methods.

SUMMARY OF THE INVENTION

The subject invention is directed to a new and useful device that expedites and automates thawing a sample of cryopreserved cells. More particularly, the subject invention is directed to an adaptor for supporting or otherwise suspending a cryovial containing a cryopreserved sample of viable cell material over a centrifuge tube containing a cell culture medium.

The adaptor has an elongated tubular body with a longitudinal axis extending therethrough. The tubular body has opposed proximal and distal ends, and an axial bore extends from the distal end thereof to the proximal end thereof to define an outer periphery of the tubular body and an inner periphery of the tubular body.

The proximal end of the tubular body includes an annular flange that extends radially outwardly from the outer periphery thereof for cooperating with a centrifuge tube into which the adaptor is inserted. The distal end of the tubular body includes an annular lip that extends radially inwardly from the inner periphery thereof for cooperating with an inverted cryovial received within the axial bore of the tubular body.

Preferably, the tubular body is formed from a polymeric material, and it has an outer diameter that is dimensioned and configured for insertion into an opening of the centrifuge tube. In addition, the tubular body has an inner diameter that is dimensioned and configured to receive the inverted cryovial. Moreover, the axial bore of the tubular body is configured to receive either an externally threaded cryovial or an internally threaded cryovial.

In the case of an internally threaded cryovial, the end of the open cryovial would abut against the annular lip formed within the axial bore of the tubular body. In the case of an externally threaded cryovial, the threaded end portion of the cryovial would extend through and out from the distal end of the adaptor and the shoulder of the cryovial behind the threaded end portion would abut or otherwise rest against the annular lip formed within the axial bore of the tubular body.

In one embodiment, the outer diameter of the tubular body at the distal end thereof is about 0.565 inches, so that a close interference fit is created between the adaptor and the centrifuge tube. Preferably, the outer diameter of the tubular body at the proximal end thereof is about 0.757 inches, so that the annular flange provides a sufficient abutment surface against the open end of the centrifuge tube when the adaptor is inserted into the tube.

The inner diameter of the tubular body at the proximal end thereof is about 0.500 inches, so that a close interference fit is created between the adaptor and the inverted cryovial when the cryovial is inserted into the axial bore of the tubular body. Preferably, the inner diameter of the tubular body at the distal end thereof is about 0.410 inches so that in the case of the internally threaded cryovial, the annular lip provides a sufficient abutment surface against the open end of the cryovial, and in the case of the externally threaded cryovial the annular lip is both sized to permits the passage of the threaded end portion and provide a sufficient abutment surface for the shoulder of the cryovial.

Those skilled in the art will readily appreciate that the dimensions set forth above, are merely exemplary, and may be altered or modified to optimally accommodate cryovials from a variety of manufactures.

The subject invention is also directed to a system for thawing a frozen specimen which includes a cryovial for containing a frozen specimen, a centrifuge tube for containing a cell growth medium, and an adaptor for suspending the cryovial over the centrifuge tube in an inverted position. Preferably, the adaptor has an elongated tubular body having a longitudinal axis extending therethrough and defining opposed proximal and distal ends. The tubular body has an axial bore extending from the distal end thereof to the proximal end thereof to define an outer periphery and an inner periphery. The outer periphery is dimensioned for insertion into the centrifuge tube and the inner periphery is dimensioned to receive the cryovial in an inverted position.

Preferably, the proximal end of the tubular body includes an annular flange that extends radially outwardly from the outer periphery thereof for cooperating with the centrifuge tube into which the adaptor is inserted, and the distal end of the tubular body includes an annular lip extending radially inwardly from the inner periphery thereof for cooperating with the cryovial received within the axial bore of the tubular body.

The subject invention is further directed to a method of thawing a frozen specimen which includes the steps of providing a centrifuge tube containing a cell growth medium, inserting an adaptor into an opening of the centrifuge tube, and inserting an inverted cryovial containing a frozen specimen into a central bore of the adaptor to suspend the cryovial over the centrifuge tube. Preferably, the method further comprises the step of loading the centrifuge tube into a centrifuge and subsequently spinning the centrifuge tube to thaw the specimen in an expeditious manner.

Similarly, the subject invention is directed to a method of thawing a frozen specimen that includes the steps of providing a centrifuge tube containing a cell growth medium, suspending an inverted cryovial containing a frozen specimen over the centrifuge tube, and spinning the centrifuge tube to thaw the frozen specimen. The method further includes the step of inserting an adaptor into an opening of the centrifuge tube to receive the inverted cryovial.

While relatively basic, the plastic adaptor of the subject invention makes a dramatic impact on the process of recovering viable cells from frozen specimens. It reduces the labor time for thawing from several minutes to a few seconds. There is virtually no labor involved, which means that a single person can load hundreds of samples within minutes (currently, this would take hours, and negatively impact the viability of the cells). The cells, once thawed, spend essentially no time in the liquid cryopreservative, since they are diluted instantly into growth medium. This process ensures the highest viability as well as recovery from each specimen, while dramatically increasing throughput. Importantly, the elimination of multiple labor-intensive steps minimizes variation in viability and yield.

These and other features of the device, system and methods of the subject invention will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the thawing system of the subject invention without undue experimentation, preferred embodiments thereof will be described in detail herein below with reference to certain figures, wherein.

DETAILED DESCRIPTION OF PREFERRED EMBODIMENTS

Figures 1, 2, 3:
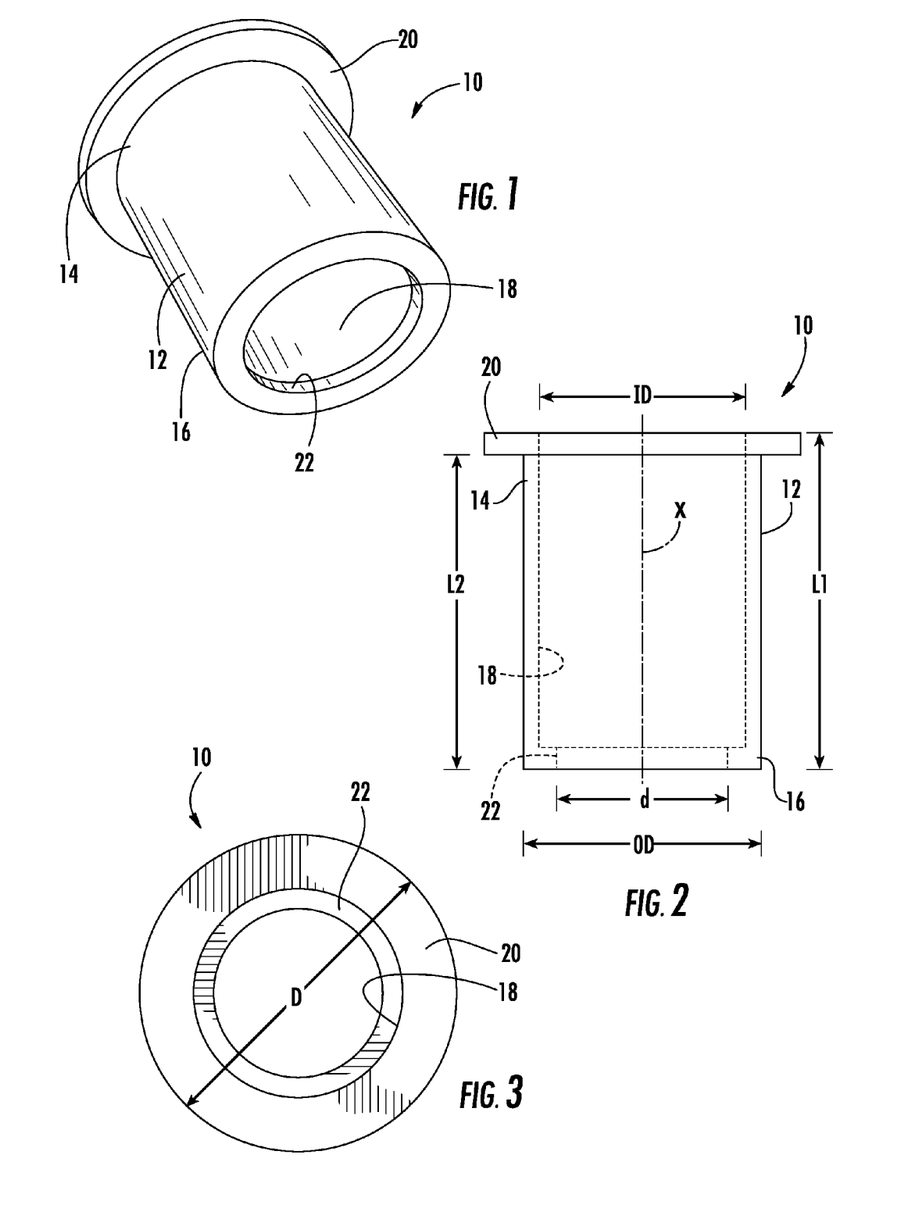
FIG. 1 is a perspective view of an adaptor constructed in accordance with a preferred embodiment of the subject invention for suspending a cryovial containing a cryopreserved sample of viable cells over a centrifuge tube containing a cell culture medium.
FIG. 2 is a side elevational view of the adaptor shown in FIG. 1, with indicia representing certain dimensional characteristics of the component.
FIG. 3 is a top plan view of the adaptor of FIG. 1, with additional dimensional indicia.

Referring now to the drawings, wherein like reference numerals identify similar structural features or aspects of the subject invention, there is illustrated in FIG. 1 a new and useful device that expedites and automates thawing of viable cryopreserved cell specimens used in a laboratory environment to perform biological research.

Figure 4:
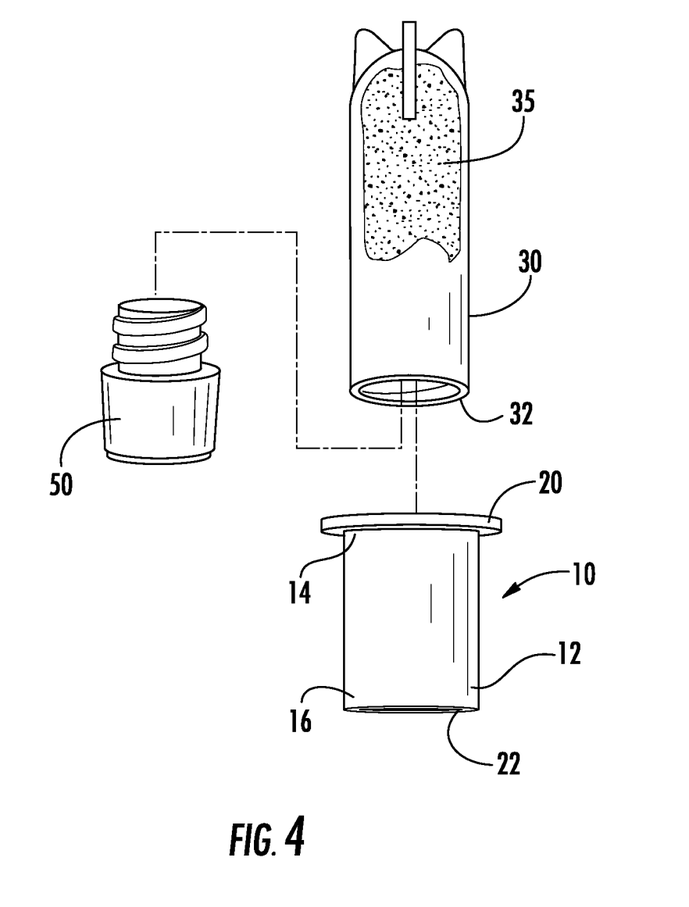
FIG. 4 is a perspective view of the adaptor of the subject invention in conjunction with an inverted internally threaded cryovial containing a cryopreserved sample of viable cells frozen sample, with its end cap removed.
Figure 5:
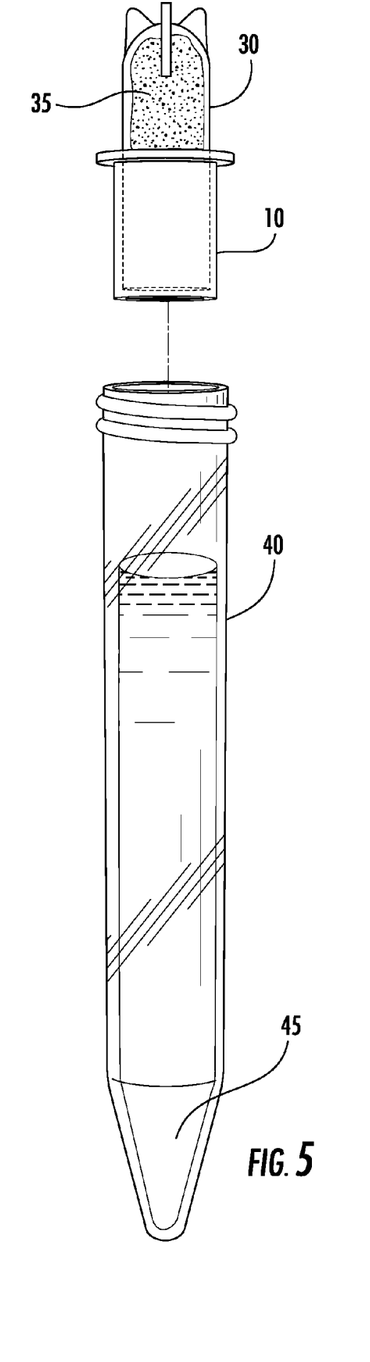
FIG. 5 is a perspective view of a centrifuge tube containing a cell culture medium and the adaptor of the subject invention spaced therefrom and supporting an inverted internally threaded cryovial, which contains a cryopreserved sample of viable cells.
Figure 6:
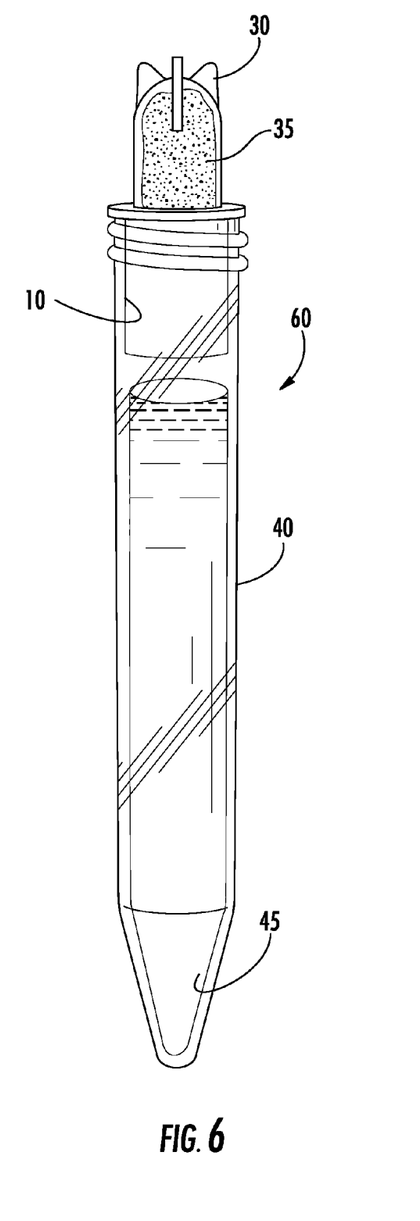
FIG. 6 is a perspective view of the assembled or integrated thawing system shown in FIG. 5, wherein the adaptor supporting the inverted internally threaded cryovial is inserted into the open end of the centrifuge tube.
Figure 9:
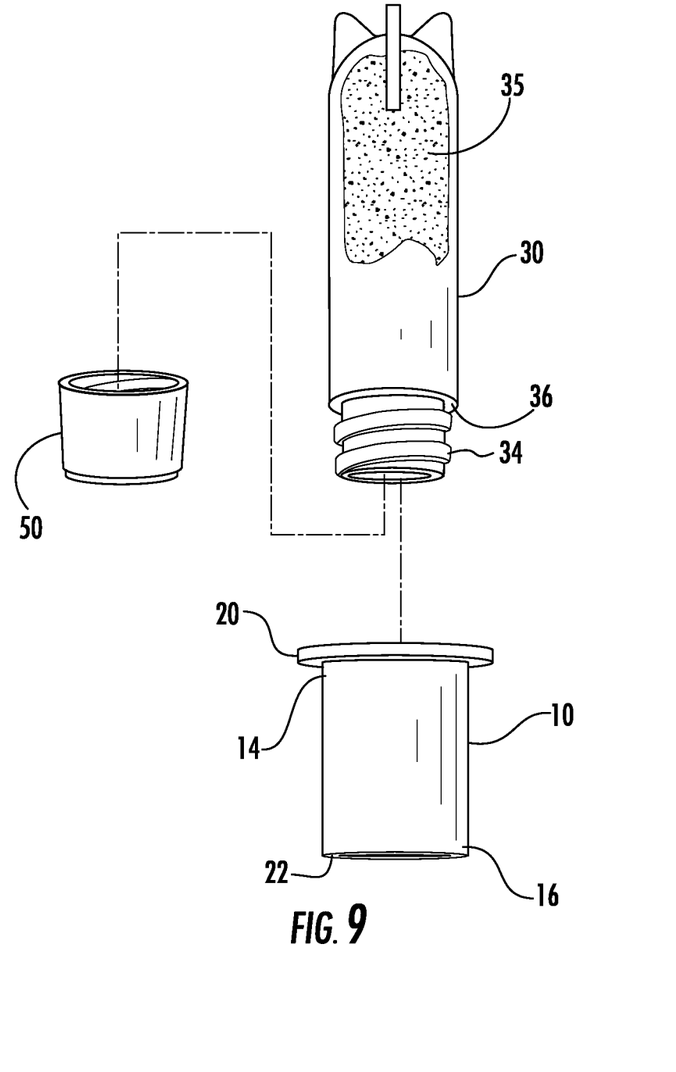
FIG. 9 is a perspective view of the adaptor of the subject invention in conjunction with an inverted externally threaded cryovial, which contains a cryopreserved sample of viable cells frozen sample, with its end cap removed.

More particularly, as best seen in FIGS. 5 and 6, the subject invention is directed to an adaptor 10 for supporting or otherwise suspending a cryovial 30 containing a frozen sample of viable cells 35 over a centrifuge tube 40 containing a warm cell culture medium 45. By way of example, the cryovial 30 may be an internally threaded cryovial as shown in FIG. 4, or the cryovial 30 may be an externally threaded cryovial as shown in FIG. 9. These differences will be discussed in greater detail herein below with respect to the construction of the adaptor 10. In either instance, the cryovial 30 contains a cell sample stored in a cryopreservative, such as, for example, DMSO or glycerol and the centrifuge tube 40 is preferably a 15 mL conical tube containing a warm cell culture medium.

Referring to FIG. 2, the adaptor 10 has an elongated tubular body 12 with a longitudinal axis "x" extending therethrough. The tubular body 12 has opposed proximal and distal ends 14 and 16, and an axial bore 18 extends from the proximal end 14 end to the distal end 16 to define an outer periphery of the tubular body 12 and an inner periphery of the tubular body 12.

Referring to FIG. 3, the proximal end 14 of the tubular body 12 includes an annular flange 20 that extends radially outwardly from the outer periphery thereof for cooperating with an upper edge of the centrifuge tube 40 into which the adaptor 10 is inserted. The distal end 16 of the tubular body 12 includes an annular lip 22 that extends radially inwardly from the inner periphery thereof for cooperating with an inverted cryovial 30 received within the axial bore 18 of the tubular body 12.

Preferably, the tubular body 12 is formed from a medical grade polymeric material to reduce heat transfer between the cryovial 30 and the centrifuge tube 40. It is envisioned however, that the adaptor 10 could be formed from a metallic material, such as, for example, stainless steel or a similar material. While there are disadvantages associated with using stainless steel rather than a polymeric material to form the adaptor (e.g., a lack of insulation between the cryovial and the tube), those skilled in the art will readily appreciate that a stainless steel or aluminum adaptor would nevertheless fall well within the scope of the subject invention, as defined by the appended claims.

Referring to FIGS. 2 and 3, the tubular body 12 of adaptor 10 has an outer diameter (O.D.) that is dimensioned and configured for insertion into an opening of the centrifuge tube 40. In addition, the tubular body 12 has an inner diameter (I.D.) that is dimensioned and configured to receive the inverted cryovial 30. Moreover, the axial bore 18 of the tubular body 12 is configured to receive either an internally threaded cryovial 30, as shown in FIG. 4, or an externally threaded cryovial 30, as shown in FIG. 9.

In the case of an internally threaded cryovial, the open end 32 of the cryovial 30 would seat against the annular lip 22 formed within the axial bore 18 of the tubular body 12, as shown for example in FIGS. 5 and 6. In the case of an externally threaded cryovial, the threaded end portion 34 of the cryovial 30 would extend out from the distal end 16 of the adaptor 10 and the shoulder 36 of the cryovial 30 behind the threaded end portion 34 would abut against the annular lip 22 formed within the axial bore 18 of the tubular body 12, as shown for example in FIGS. 10 and 11.

Referring back to FIGS. 2 and 3, the outer diameter (O.D.) of the tubular body 12 at the distal end 16 thereof is about 0.565 inches, so that a close interference fit is created between the adaptor 10 and the centrifuge tube 40. This will ensure that the adaptor 10 is securely engaged in the centrifuge tube 40 while it is spinning in a centrifuge during the thawing process. Preferably, the outer diameter (D) of the tubular body 12 at the proximal end 14 thereof is about 0.757 inches so that the annular flange 20 provides a sufficient abutment surface against the open end of the centrifuge tube 40, as best seen in FIG. 6.

The inner diameter (I.D.) of the tubular body 12 at the proximal end 14 thereof is about 0.500 inches, so that a close interference fit is created between the adaptor 10 and the inverted cryovial 30. This will ensure that the cryovial 30 is securely supported over centrifuge tube 40 while it is spinning in a centrifuge during the thawing process. Preferably, the inner diameter (d) of the tubular body 12 at the distal end thereof is about 0.410 inches.

Figure 10:
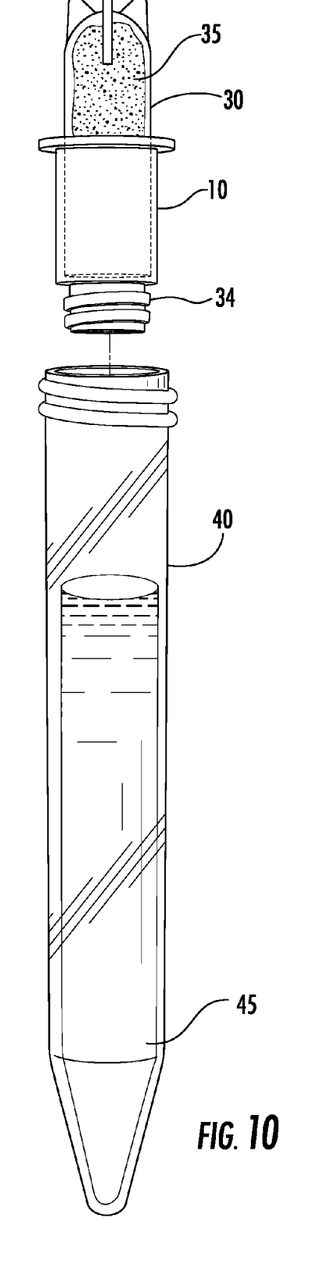
FIG. 10 is a perspective view of a centrifuge tube containing a cell culture medium and the adaptor of the subject invention spaced therefrom and supporting an inverted externally threaded cryovial containing a cryopreserved sample of viable cells.
Figure 11:
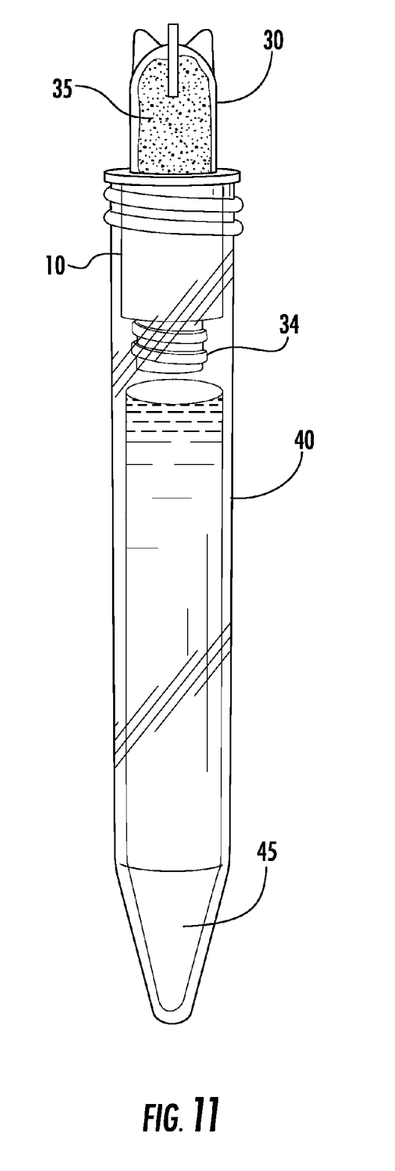
FIG. 11 is a perspective view of the assembled thawing system shown in FIG. 10, wherein the adaptor supporting the inverted externally threaded cryovial is inserted into the open end of the centrifuge tube.

Thus, in the case of the internally threaded cryovial 30 shown in FIG. 4, the annular lip 22 at the distal end of the axial bore 18 of the adaptor 10 provides a sufficient abutment surface against the open end of the cryovial 30, as best seen in FIGS. 5 and 6. In the case of the externally threaded cryovial 30 shown in FIG. 9, the annular lip 22 at the distal end of the axial bore 18 of the adaptor 10 is both sized to permit the passage of the threaded end portion 32 of cryovial 30 and provide a sufficient abutment surface for the shoulder 34 of cryovial 30, as shown in FIGS. 10 and 11.

With continuing reference to FIG. 2, the tubular body 12 of the adaptor 10 has an overall axial length (L1) of about 0.800 inches and its axial length (L2) measured from below the flange of about 0.750 inches. This will ensure that there is sufficient purchase of the adaptor 10 by the open end of the centrifuge tube 40.

Referring now to FIGS. 4 through 8, the subject invention is further directed to a novel method of thawing viable cryopreserved cell specimens. The method includes the steps of: a) providing a cryovial 30 (internally threaded or externally threaded) containing a viable cryopreserved cell specimen 35; b) providing a centrifuge tube 40 containing a warm cell culture medium 45; c) removing the threaded end cap 50 from the cryovial 30; d) inserting the opened cryovial 30 into the axial bore 18 of adaptor 10 in an inverted position, until the front end 32 of the cryovial 30 abuts against the annual lip 22 at the distal end of the axial bore of the adaptor 10; e) inserting the adaptor 10 into the opening of the centrifuge tube 40 until the annular flange 20 at the proximal end of the adaptor 10 abuts against the upper edge of the centrifuge tube 40, thereby forming an integral unit 60 in which the cryovial 30 is firmly suspended over the centrifuge tube 40, as shown in FIG. 6.

Figure 7:
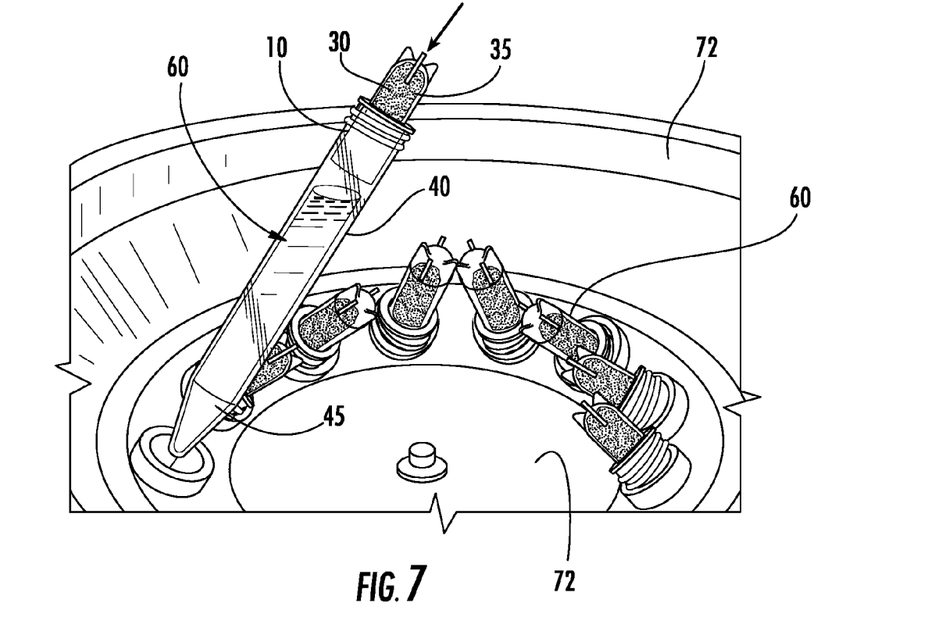
FIG. 7 illustrates the integrated thawing system of FIG. 6 being loaded into a centrifuge, with a plurality of other similarly assembled units.
Figure 8:
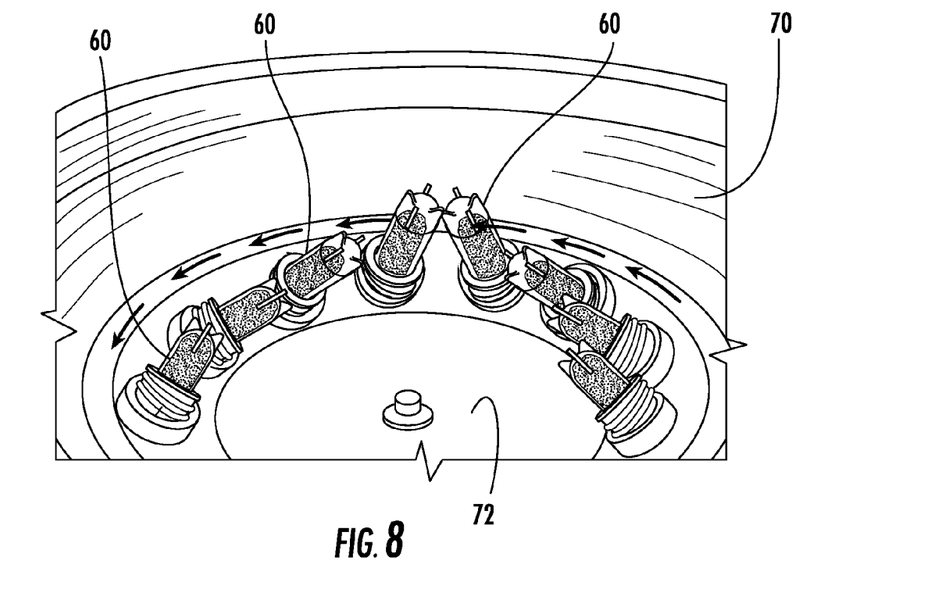
FIG. 8 illustrates a fully loaded centrifuge in operation to simultaneously thaw a plurality of cryopreserved samples.

The method further includes the steps of preparing a plurality of assembled units 60 in the manner described above, loading each of the assembled units 60 into a bucket 72 of a centrifuge 70, as shown in FIG. 7, and then subsequently spinning the plurality of assembled units 60 in the centrifuge 70 for a predetermined period of time to thaw the specimens together in a uniform and expeditious manner, as illustrated in FIG. 8.

The cells, once thawed, spend virtually no time in the cryopreservative, as they are diluted instantly into the cell culture medium 45 in the tube 40. This process ensures the highest degree of cell viability as well as recovery from each specimen, with virtually no labor required. By accelerating the thawing process and removing the labor component, the process becomes far more reproducible and yields far better results than traditional thawing methods know in the art. This can significantly impact immunoassays and bioassays in the clinical, clinical research and research settings, by improving quality and throughput.

Those skilled in the art will readily appreciate that the cryovial 30, adaptor 10, and centrifuge tube 40 can be assembled quickly into a single unit 60 and fit easily into a centrifuge bucket 72. The height of the assembled unit 60 will not interfere with the lid of the centrifuge 70. Unlike traditional thawing methods used in most laboratories, use of the adaptor 10 does not require the use of a 37° C. water bath. The cryovials 30 of cryopreserved cells are taken directly from the freezer (or a box of dry ice), uncapped, placed in the adaptor 10, and then suspended over a 15 mL conical tube 40 containing warm cell culture medium.

The time needed for these steps is relatively small, so as many as forty-eight (48) cryovials (the typical capacity of a single centrifuge) can be processed at one time. During centrifugation, frozen cells are slowly dislodged from the cryovial 30, falling into the warm media 45 contained in the centrifuge tube 40 and are immediately diluted out of the toxic cryopreservative under centrifugal force. In the warm media, the cells safely transition from frozen ice crystals into liquid suspension, moving out of the toxic cryoprotectant (DMSO) at the top of the tube and into 100% media at the bottom of the tube. This minimizes the time and exposure to the toxic cryopreservative.

Through experimentation, it has been shown that a single lab technician, working with one centrifuge, requires about one hour to process 15 frozen cryovials using extant techniques. It has also been shown that 30 frozen cryovials can be processed in about one hour when two lab technicians are working together with two centrifuges side by side. However, this increases manpower and equipment needs and can result in variable thawing as the work is still performed in batches of four to eight vials at a time. It has been shown that using the adaptor 10 of the subject invention, one technician can process nearly one hundred cryopreserved cell samples (if two centrifuges are available), with very little set up time in less than 20 minutes.

In sum, the adaptor 10 of the subject invention automates and standardizes the thawing process for cryopreserved cell specimens, which is a fundamental laboratory task. The methods of the subject invention avoid the variability of classical methods, in which the length of thawing time can differ by batch or technician. Additionally, since a water bath is not needed, the risk of sample contamination is decreased and throughput is increased.

While the subject invention has been shown and described with reference to preferred embodiments and methods, those skilled in the art will readily appreciate that various changes and/or modifications may be made thereto without departing from the spirit and scope of the subject invention as defined by the appended claims.

What is claimed is:

1. An adaptor for suspending an inverted cryovial containing a frozen specimen over a centrifuge tube comprising: an elongated tubular body having a longitudinal axis extending therethrough and defining opposed proximal and distal ends, the tubular body having an axial bore extending from the distal end thereof to the proximal end thereof to define an outer periphery of the tubular body and an inner periphery of the tubular body, the proximal end of the tubular body including an annular flange extending radially outwardly from the outer periphery thereof and configured for abutting against an upper edge of a centrifuge tube into which the adaptor is inserted, and the distal end of the tubular body including an annular lip extending radially inwardly from the inner periphery thereof and configured for abutment with a front end of an inverted cryovial received within the axial bore of the tubular body, wherein the axial bore of the tubular body has a uniform inner diameter extending from the proximal end of the tubular body to the annular lip at the distal end of the tubular body.

2. An adaptor as recited in claim 1, wherein the tubular body is formed from a polymeric material.

3. An adaptor as recited in claim 1, wherein the tubular body has an outer diameter that is dimensioned and configured for insertion into an opening of the centrifuge tube.

4. An adaptor as recited in claim 1, wherein the tubular body has an inner diameter that is dimensioned and configured to receive the inverted cryovial.

5. An adaptor as recited in claim 3, wherein the outer diameter of the tubular body at the proximal end thereof is about 0.757 inches.

6. An adaptor as recited in claim 3, wherein the outer diameter of the tubular body at the distal end thereof is about 0.565 inches.

7. An adaptor as recited in claim 4, wherein the inner diameter of the tubular body at the proximal end thereof is about 0.500 inches.

8. An adaptor as recited in claim 4, wherein the inner diameter of the tubular body at the distal end thereof is about 0.410 inches.

9. An adaptor as recited in claim 1, wherein the tubular body has an axial length of about 0.800 inches.

10. An adaptor as recited in claim 1, wherein the tubular body has an axial length measured from below the flange of about 0.750 inches.

11. An adaptor for suspending an inverted cryovial over a centrifuge tube comprising:
an elongated tubular body having an outer periphery with an outer diameter that is dimensioned and configured for insertion into an open end of a centrifuge tube, the tubular body having a longitudinal axis extending therethrough and defining opposed proximal and distal ends, the tubular body having an axial bore extending therethrough from the proximal end thereof to the distal end thereof which defines an inner periphery with an inner diameter that is dimensioned to receive an inverted cryovial containing a frozen specimen, a distal end of the axial bore including an annular lip extending radially inwardly from the inner periphery thereof and configured for abutment with a front end of the inverted cryovial received within the axial bore of the tubular body, wherein the axial bore of the tubular body has a constant inner diameter extending from the proximal end of the tubular body to the annular lip at the distal end of the axial bore.

12. An adapter as recited in claim 11, wherein the proximal end of the tubular body includes an annular flange extending radially outwardly from the outer periphery thereof and configured to abut against an upper edge of the centrifuge tube into which the tubular body is inserted.

* * * * *